(12) United States Patent
Kumar et al.

(10) Patent No.: US 9,145,368 B2
(45) Date of Patent: Sep. 29, 2015

(54) ORGANOCATALYTIC SYNTHESIS OF CHIRAL PYRAZOLIDINES AND THEIR ANALOGUES

(71) Applicant: COUNCIL OF SCIENTIFIC & INDUSTRIAL RESEARCH, New Delhi (IN)

(72) Inventors: Boopathi Senthil Kumar, Pune (IN); Vaithiyanathan Venkataramasubramanian, Pune (IN); Arumugam Sudalai, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/365,539

(22) PCT Filed: Dec. 17, 2012

(86) PCT No.: PCT/IN2012/000824
§ 371 (c)(1),
(2) Date: Jun. 13, 2014

(87) PCT Pub. No.: WO2013/088456
PCT Pub. Date: Jun. 20, 2013

(65) Prior Publication Data
US 2014/0357872 A1 Dec. 4, 2014

(30) Foreign Application Priority Data
Dec. 15, 2011 (IN) .......................... 3657/DEL/2011

(51) Int. Cl.
*C07D 231/04* (2006.01)

(52) U.S. Cl.
CPC ................................... *C07D 231/04* (2013.01)

(58) Field of Classification Search
CPC ..................................................... C07D 231/04
See application file for complete search history.

(56) References Cited

PUBLICATIONS

International Preliminary Report on Patentability including Written Opinion mailed on Jun. 26, 2014 for corresponding International Application No. PCT/IN2012/000824, 7pp.
Ahn, Jin Hee et al.; "Synthesis and evaluation of pyrazolidine derivatives as dipeptidyl peptidase IV (DP-IV) inhibitors"; Bioorganic & Medicinal Chemistry Letters; 15; 2005; pp. 1337-1340.
Giampietro, Natalie C. et al.; "Stereoselective Synthesis of cis- or trans-3,5-Disubstitued Pyrazolidines via Pd-Catalyzed Carboamination Reactions: Use of Allylic Strain to Control Product Stereochemistry Through N-Substituent Manipulation"; J. Am. Chem. Soc.; 2008; 130; pp. 12907-12911.
Kumar, B. Senthil et al.; "Organocatalytic Sequential α-Amination/Corey-Chaykovsky Reaction of Aldehydes: A High Yield Synthesis of 4-Hydroxypyrazolidine Derivatives"; American Chemical Society; Organic Letters; 2012; vol. 14; No. 10; pp. 2468-2471.

*Primary Examiner* — Samantha Shterengarts
(74) *Attorney, Agent, or Firm* — Christie, Parker & Hale, LLP

(57) ABSTRACT

Disclosed herein is a highly enantio- (75 to 98% ee) and diastereoselective (99 to 100% de) synthesis of functionalized pyrazolidines via tandem a-amination-Corey Chaykovsky reaction of alpha unsubstituted aldehydes.

7 Claims, 1 Drawing Sheet

ORGANOCATALYTIC SYNTHESIS OF CHIRAL PYRAZOLIDINES AND THEIR ANALOGUES

CROSS-REFERENCE TO RELATED APPLICATIONS

Figure 1:
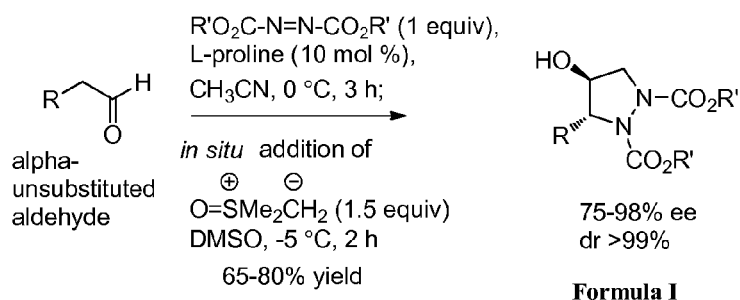
Figure 2:
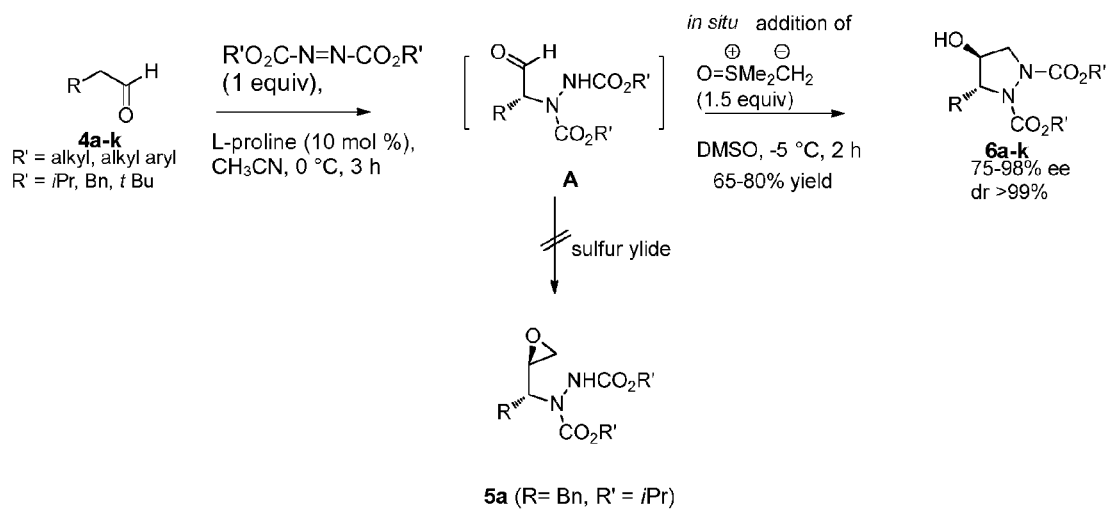

This application is a National Phase Patent Application and claims priority to and benefit of International Application Number PCT/IN2012/000824, filed on Dec. 17, 2012, which claims priority to and benefit of Indian Patent Application Number 3657/DEL/2011, filed on Dec. 15, 2011, the entire disclosures of which are incorporated herein by reference.

FIELD OF THE INVENTION

This invention relates to a highly enantio- and diastereoselective synthesis of functionalized pyrazolidines of formula I via tandem α-amination-Corey Chaykovsky reaction of aldehydes. The reaction allows the creation of three covalent bonds and two contiguous chiral centers in excellent enantio and diastereoselectivity with highly atom-economic transformation in a single step.

BACKGROUND AND PRIOR ART OF THE INVENTION

Many analgesic/anti-inflammatory drug molecules such as Ampyrone, Azapropazone, Clofezone, Kebuzone, Metamizole, Mofebutazone, Oxyphenbutazone, Phenazone, Phenylbutazone, Phenylbutazone, Sulfinpyrazoneetc possesses pyrazolidine ring in the structure.

There is ample literature available on the preparation and evaluation of pharmacological activity of the compounds containing pyrazolidine scaffold. There is considerable research activity in progress for the synthesis and evaluation of the new molecules with pyrazolidine scaffold for various biological activities as well as novel methods of synthesis for achieving the same.

References may be made to Journal "Biochemical Pharmacology 70 (2005) 22-29", wherein Inhibition of dipeptidyl peptidase IV by novel inhibitors with pyrazolidine scaffold is reported by HyaeGyeongCheonin.

References may be made to Journal, Bioorganic & Medicinal Chemistry Letters Volume 15, Issue 5, 1 Mar. 2005, Pages 1337-1340, wherein Jin Hee Ahn et al reported new series of pyrazolidine derivatives and their ability to inhibit dipeptidyl peptidase IV (DP-IV).

References may be made to U.S. Pat. No. 7,557,102, which discloses Pyrazolidine-1,2-dicarboxyldiphenylamide derivatives as coagulation factor Xa inhibitors for the treatment of thrombosis.

References may be made to Journal, *Bioorganic & Medicinal Chemistry Letters*, 2005, 15, 2527-2531 Kristina M. K. Kutterer et al discloses 4-alkyl and 4,4-dialkyl 1,2-bis(4-chlorophenyl)pyrazolidine-3,5-dione derivatives were synthesized, utilizing microwave accelerated synthesis, for evaluation as new inhibitors of bacterial cell wall biosynthesis.

References may be made to Journal J. Am. Chem. Soc., 2008, 130 (39), pp 12907-12911, wherein stereoselective Synthesis of cis- or trans-3,5-Disubstituted Pyrazolidines via Pd-Catalyzed Carboamination Reactions of unsaturated hydrazine derivatives is reported by Natalie C. The products obtained are reported to be in good yield with up to >20:1 diastereoselectivity.

In the light of the above, it is evident that the compounds having pyrazolidine ring possess valuable biological activities and therefore, it is essential to have an industrially viable process to synthesize the same on larger scale. As mentioned above, metal catalyzed reaction for the synthesis of Pyrazolidines are known, however, the same incurs higher cost and further affects the nature due to the pollution.

OBJECTS OF THE INVENTION

Main objective of the present invention is to develop an efficient, cost effective and pollution free organocatalysis for the synthesis of functionalised pyrazolidines, that is free from the use of metal catalysts.

SUMMARY OF THE INVENTION

Accordingly, the current inventors have developed hitherto unexploited and alternate, highly enantio- and diastereoselective synthesis for functionalised pyrazolidines via tandem α-amination-Corey Chaykovsky reaction of aldehydes in one pot. The instant process makes contribution to green chemistry by avoiding metal-based catalysis.

Present invention provides a process for synthesis of functionalised pyrazolidines of formula I with enatioselectivity in the range of 75 to 98% ee and distereoselectivity in the range of 99 to 100% de

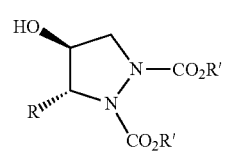

Formula I wherein, R is selected from the group consisting of H, halogen, C1 to C10 branched or unbranched alkyl, C1 to C10 cycloalkyl which may optionally be substituted with halo, —OH; aryl which may optionally be as mono or di or tri substituted by halo, hydroxy, nitro, amino, CN, COOH, CONH2, heteroaryl with N, O and/or S atoms as hetero atoms, naphthyl, which may optionally be substituted with halo, hydroxy, nitro, amino, CN, COOH, CONH2, and R' is selected from ter-butyl, iso-propyl and benzyl groups, via tandem α-amination-Corey Chaykovsky reaction of aldehydes and the said process comprising the steps of:

a) reacting an alpha-unsubstituted aldehyde with azodicarboxylates at a temperature in the range of 0 to 20° C. in presence of L-proline in a solvent to obtain α-hydrazino aldehydes; and b) subjecting the α-hydrazino aldehydes to Corey Chaykovsky reaction in situ at a temperature in the range of (−)4 to (−)6° C. to obtain functionalised pyrazolidines of formula I.

In an embodiment of the present invention, alpha-unsubstituted aldehydes are selected from the group consisting of benzylaldehyde, 3,4-di methylbenzylaldehyde, 3,4-methylenedioxybenzylaldehyde, 2-Br-4,5-methylenedioxybenzylaldehyde, 2-CN-4,5-methylenedioxybenzylaldehyde, naphthalene-1-yl-methylaldehyde, 2-NO2-4,5-dimethoxybenzylaldehyde, n-butylaldehyde, 4-azidopropylaldehyde, 3-benzyloxymethylaldehyde, and 3-benzyloxypropylaldehyde.

In yet another embodiment of the present invention, the azodicarboxylates are selected from the group consisting of diisopropyl azodicarboxylates, ditert-butyl azodicarboxylates and dibenzyl azodicarboxylates.

In yet another embodiment of the present invention, the solvent used is selected from the group consisting of cyclic carbonates, chlorinated solvents, nitriles, N,N-dimethylformamide (DMF) or Dimethyl sulfoxide (DMSO).

In yet another embodiment of the present invention, solvent used is a nitrile, preferably acetonitrile.

In yet another embodiment of the present invention, the Corey Chaykovsky reaction is conducted in presence of dimethyloxosulfonium methylide in Dimethyl sulfoxide (DMSO).

DETAILED DESCRIPTION OF THE INVENTION

In accordance with the above object, the present invention discloses highly enantio- and diastereoselective synthesis of functionalized pyrazolidines of formula I via tandem α-amination-Corey Chaykovsky reaction of aldehydes. The reaction allows the creation of three covalent bonds and two contiguous chiral centers in excellent enantio and diastereoselectivity in single step.

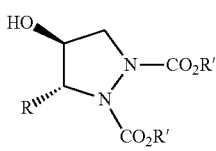

Formula I wherein

R is selected from the group consisting of H, halogen, C1 to C10 branched or unbranched alkyl, C1 to C10 cycloalkyl which may optionally be substituted with halo, —OH; aryl which may optionally be as mono or di or tri substituted by halo, hydroxy, nitro, amino, CN, COOH, CONH2, etc., hetero aryl with N, O and/or S atoms as hetero atoms, naphthyl, which may optionally be substituted with halo, hydroxy, nitro, amino, CN, COOH, CONH2, etc; and R' is selected from ter-butyl, iso-propyl or benzyl groups.

The instant invention utilizes commercially available L-Proline as an inexpensive catalyst, simple and easily available starting materials to obtain the functionalized pyrazolidines of formula I in high yield with excellent enantio- and diastereoselectivity.

The invention provides a process for synthesis of functionalized pyrazolidines of formula I via tandem α-amination-Corey Chaykovsky reaction of alpha unsubstituted aldehydes, which comprises L-proline catalyzed α-Amination of aldehyde to obtain α-hydrazino aldehydes, which on Corey Chaykovsky reaction in presence of sulfurylide to yield pyrazolidines by ring cyclization. The reaction proceeds with various azodicarboxylates as the nitrogen source, to yield functionalized pyrazolidines of formula I in high yields and excellent enantioselectivities as shown in scheme 1.

Accordingly, the synthesis of functionalized pyrazolidines of formula I of the present invention comprises alpha-amination of aldehyde in presence of L-proline to obtain corresponding R-amino aldehyde insitu. As this amino-aldehyde is prone to racemization under basic conditions, an effective reaction conditions were developed to carry out the Corey Chaykovsky reaction by conducting the reaction under various temperature conditions. The addition of the sulfurylide to R-amino aldehyde at 25° C. gave the corresponding pyrazolidine as a single diastereomer in 80% yield with 5% ee (low % ee is probably due to racemization).

However, a remarkable improvement in enantioselectivity (75% ee) was realized when the reaction is performed at 10° C. for 2 h. The best results are achieved when the addition of ylide is conducted at (−)5° C. (91% ee with 73% yield). However, further lowering of the temperature to either (−)20° C. or (−)40° C., a deleterious effect on both the yield and enantioselectivity was observed. The optimization of the reaction conditions as discussed above are depicted in table 1.

The invention discloses a synthesis for functionalised pyrazolidines of formula I via tandem α-amination-Corey Chaykovsky reaction of aldehydes comprising:

a) Reacting an alpha-unsubstituted aldehyde with azodicarboxylates in presence of L-proline to obtain α-hydrazino aldehydes; and b) Subjecting the α-hydrazino aldehydes to Corey Chaykovsky reaction to obtain functionalised pyrazolidines of formula I.

The reaction of step a) proceeds at a temperature of 0° C. to (−)5° C. with azodicarboxylates as the nitrogen source in a solvent medium selected from cyclic carbonates, chlorinated solvents, nitriles etc. one preferred solvent for the purpose of proline catalyzed amination is acetonitrile. The Corey Chaykovsky reaction according to the invention is conducted at a temperature of (−) 5° C. in presence of dimethyloxosulfonium methylide in DMSO.

The in situ trapping of alpha amino aldehydes according to the invention with dimethyloxosulfonium methylide is shown as scheme 2.

The preparation of sulfurylide solution comprises addition of NaH (previously washed with petroleum ether to remove oil) to dry DMSO (10 mL) under stirring at 25° C. in N2 atmosphere followed by addition of trimethyloxosulfonium iodide over a period of 5 min via a solid addition funnel until it became a homogenous solution.

The sequential procedure for alpha-Amination/Corey Chaykovsky Reaction of Aldehydes involves reaction of alpha-unsubstituted aldehyde (4a-k) with azadicarboxylate and L-proline in dry CH$_3$CN at 0° C. under stirring for 3 h followed by addition of a solution of dimethyloxosulfonium methylide in DMSO at (−)5° C. and further stirred for 2 h at the same temperature. The progress of the reaction was monitored by TLC followed by quenched the reaction mass by the addition of an aq. NH$_4$Cl solution. The reaction mixture was concentrated in vacuum to remove acetonitrile and the concentrate was extracted with diethyl ether. The combined organic layers were washed with brine, dried over anhyd. Na$_2$SO4, and concentrated under reduced pressure to give the crude products, which were then purified by flash column chromatography (100-200 mesh) using petroleum ether and ethyl acetate as eluents to afford the pure Chiral Pyrazolidines (6a-k).

Thus the instant invention provides excellent synthetic route for the preparation of functionalized pyrazolidines via tandem α-amination-Corey Chaykovsky reaction of aldehydes in high yields with excellent diastereo and enantioselectivities. The synthesis according to the invention is devoid of metal catalyst and involves organocatalysis. Also, the instant reaction is advantageous being one pot with the creation of two chiral centers in single step. The yields of the functionalized pyrazolidines are in the range of 75-85%, with high diastereo (de>99%) and enantioselectivities (ee>90%). Further, the instant invention encompasses the preparation of pharmaceutically usable derivatives such as salts, solvates and stereoisomers thereof, including mixtures thereof in all ratios.

Also, the instant method of synthesis has excellent Functional group tolerance and hence easier to adopt for the synthesis of variousbiologically active compounds such as anti-thrombotic, anti-bacterial, anti-pyretic, anti-depressant molecules, etc. Also, the instant invention is cost-effective as it involves simple and cheaper starting materials.

The invention provides optimization of the temperature of the instant reaction by conducting the reaction at various temperature conditions and the results of which are depicted in table 1. According to the results presented in table 1, the temperature of the instant invention is optimized at −5° C. to achieve functionalized pyrazolidines with excellent diastereo and enantioselectivities.

In another aspect, the invention provides the optimization of the reaction with Azodicarboxylates at different temperatures and found that the temperature of the instant invention can be optimized at (−)5° C. to achieve functionalized pyrazolidines with excellent diastereo and enantioselectivities as shown in table 1.

TABLE 1

Proline-Catalyzed α-Amination/Corey Chaykovsky Reaction of Hydrocinnamaldehyde[a] is shown in table 1

$R'O_2C-N=N-CO_2R'$ (1 equiv.),
L-proline (10 mol %),
$CH_3CN$, 0° C., 3 h;
in situ additon of
$O=SMe_2CH_2$ (1.5 equiv),
DMSO, temp, 2 h 4a (R = Bn)

6a (R = Bn)

| no. | amine (R') | temp (° C.) | yield of 6a (%)[b] | ee (%)[c] | de (%)[d] |
|---|---|---|---|---|---|
| 1 | iPr | 25 | 80 | 5 | 99 |
|   |     | 10 | 75 | 75 | 99 |
|   |     | −5 | 73 | 91 | 99 |
|   |     |    | (45)[e] | (79)[e] |  |
|   |     | −20 | 52 | 88 | 99 |
|   |     | −40 | 48 | 84 | 99 |
| 2 | Bn  | −5 | 71 | 90 | 100 |
| 3 | tBu | −5 | 60 | 80 | 100 |

[a]aldehyde (5 mmol), amine (R'O₂C—N=N-CO₂R') (5 mmol), L-proline (10 mol %), , dimethyloxosulfonium methylide (7.5 mmol).
[b]isolated yield after column chromatographic purification.
[c]determined from chiral HPLC analysis (Chiracel OD-H, Whelk-01columns; n-hexane/2-propanol).
[d]Product is obtained as a single diastereomer as determined from ¹H, ¹³C NMR and HPLC analysis.
[e]refers to 2-[bis(3,5-bistrifluoromethylphenyl)trimethylsilanyloxymethyl]pyrro-lidine is used as catalyst.

Alpha-unsubstituted aldehydes bearing bromo, cyano, nitro, methoxy, and methylene-dioxy groups on the aromatic nucleus and azide and benzyl ether substitutions in aliphatic compounds were well-tolerated under the reaction conditions. For all the cases studied, the products 6a-k were indeed obtained in high yields (65-80%) and excellent enantioselectivities (75-98% ee) with de >99% as shown in table 2.

TABLE 2

Various Chiral Pyrazolidines (6a-6k) synthesized by Proline-Catalyzed Asymmetric Tandem α-Amination/Corey Chaykovsky Reaction[a] according to the invention

| no. | substrates 4a-k (R) | amine (R') | products[a] 6a-k yield (%)[b] | ee (%)[c] |
|---|---|---|---|---|
| 1 | benzyl (4a) | iPr | 73 | 91 |
| 2 | 3,4-dimethylbenzyl (4b) | iPr | 71 | 94 |
| 3 | 3,4-methylenedioxybenzyl (4c) | Bn | 80 | 90 |
| 4 | 2-Br-4,5-methylenedioxybenzyl (4d) | iPr | 74 | 95 |
| 5 | 2-CN-4,5-methylenedioxybenzyl (4e) | iPr | 75 | 75 |
| 6 | naphthalene-1-yl-methyl (4f) | iPr | 70 | 90 |
| 7 | 2-NO₂-4,5-dimethoxybenzyl (4g) | iPr | 68 | 90 |
| 8 | n-butyl (4h) | Bn | 65 | 92 |
| 9 | 4-azidopropyl (4i) | Bn | 66 | 91 |
| 10 | 3-benzyloxymethyl (4j) | Bn | 70 | 90 |
| 11 | 3-benzyloxypropyl (4k) | iPr | 72 | 98 |

[a]aldehyde (5 mmol), amine source (R'O₂C—N=N—CO₂R') (5 mmol), L-proline (10 mol %), dimethyloxosulfonium methylide (7.5 mmol).
[b]isolated yield after column chromatographic purification.
[c]determined from chiral HPLC analysis (Chiracel OD-H, Whelk-01column; n-hexane/2-propanol).

EXAMPLES

Following examples are given by way of illustration and therefore should not be construed to limit the scope of the invention.

General Experimental Procedure

Example 1

Preparation of Sulfurylide 0.18 g (7.5 mmol) of NaH (previously washed with petroleum ether to remove oil) was added to an oven-dried three-necked flask, followed by the addition of dry DMSO (10 mL) through a septum to it, and the whole slurry was stirred at 25° C. under a $N_2$ atmosphere. Then trimethyloxosulfonium iodide (1.67 g, 7.5 mmol) was added to the slurry over a period of 5 min via a solid addition funnel until it became a homogenous solution.

Example 2

Procedure for Sequential α-Amination/Corey Chaykovsky Reaction of Aldehydes

To a cooled solution of azadicarboxylate (5.0 mmol) and L-proline (10 mol %) in dry $CH_3CN$ (20 ml) at 0° C. was added alpha-unsubstituted aldehyde (4a-k, 5 mmol), and the mixture was stirred for 3 h at 0° C. This was followed by the addition of a solution of dimethyloxosulfonium methylide in DMSO at −5° C. and allowed to stir for 2 h at the same temperature. The progress of the reaction can be monitored by TLC. It was then quenched by the addition of an aq. $NH_4Cl$ solution. The mixture was concentrated in vacuum to remove acetonitrile and the concentrate was extracted with diethyl ether (3×40 mL). The combined organic layers were washed with brine, dried over anhyd. $Na_2SO_4$, and concentrated under reduced pressure to give the crude products, which were then purified by flash column chromatography (100-200 mesh) using petroleum ether and ethyl acetate as eluents to afford the pure Chiral Pyrazolidines (6a-k).

Advantages of the Invention

The salient features of the methodology are as follows: (1) metal-free synthesis, (2) milder reaction conditions, (3) functional group tolerance, and (4) high yields with excellent enantio- and diastereoselectivity.

The invention claimed is:

1. A process for synthesis of functionalised pyrazolidines of formula I with enantioselectivity in the range of 75 to 98% ee and diastereoselectivity in the range of 99 to 100% de

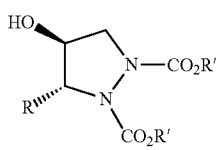

Formula I wherein, R is selected from the group consisting of H, halogen, C1 to C10 branched or unbranched alkyl, C1 to C10 cycloalkyl which may optionally be substituted with halo, —OH; aryl which may optionally be as mono or di or tri substituted by halo, hydroxy, nitro, amino, CN, COOH, CONH$_2$, heteroaryl with N, O and/or S atoms as hetero atoms, naphthyl, which may optionally be substituted with halo, hydroxy, nitro, amino, CN, COOH, CONH2, and R' is selected from ter-butyl, isopropyl and benzyl groups, via tandem α-amination-Corey Chaykovsky reaction of α-hydrazino aldehydes and the said process comprising the steps of:

a) reacting an alpha-unsubstituted aldehyde with azodicarboxylates at a temperature in the range of 0 to 20° C. in presence of L-proline in a solvent to obtain α-hydrazino aldehydes; and b) subjecting the α-hydrazino aldehydes to Corey Chaykovsky reaction insitu at a temperature in the range of (−)4 to (−)6° C. to obtain functionalised pyrazolidines of formula I.

2. The process as claimed in step (a) of claim 1, wherein the alpha-unsubstituted aldehydes are selected from the group consisting of benzylaldehyde, 3,4-dimethylbenzylaldehyde, 3,4-methylenedioxybenzylaldehyde, 2-Br-4,5-methylenedioxybenzylaldehyde, 2-CN-4,5-methylenedioxybenzylaldehyde, naphthalene-1-yl-methylaldehyde, 2-NO2-4,5-dimethoxybenzylaldehyde, n-butylaldehyde, 4-azidopropylaldehyde, 3-benzyloxymethylaldehyde, and 3-benzyloxypropylaldehyde.

3. The process as claimed in step (a) of claim 1, wherein the azodicarboxylates are selected from the group consisting of diisopropyl azodicarboxylates, ditert-butyl azodicarboxylates and dibenzyl azodicarboxylates.

4. The process as claimed in step (a) of claim 1, wherein the solvent used is selected from the group consisting of cyclic carbonates, chlorinated solvents, nitriles, N,N-dimethylformamide (DMF) or Dimethyl sulfoxide (DMSO).

5. The process as claimed in claim 4, wherein solvent used is a nitrile.

6. The process as claimed in step (b) of claim 1, wherein the Corey Chaykovsky reaction is conducted in presence of dimethyloxosulfonium methylide in Dimethyl sulfoxide (DMSO).

7. The process as claimed in claim 5, wherein the nitrile is acetonitrile.

* * * * *